Figure 1:
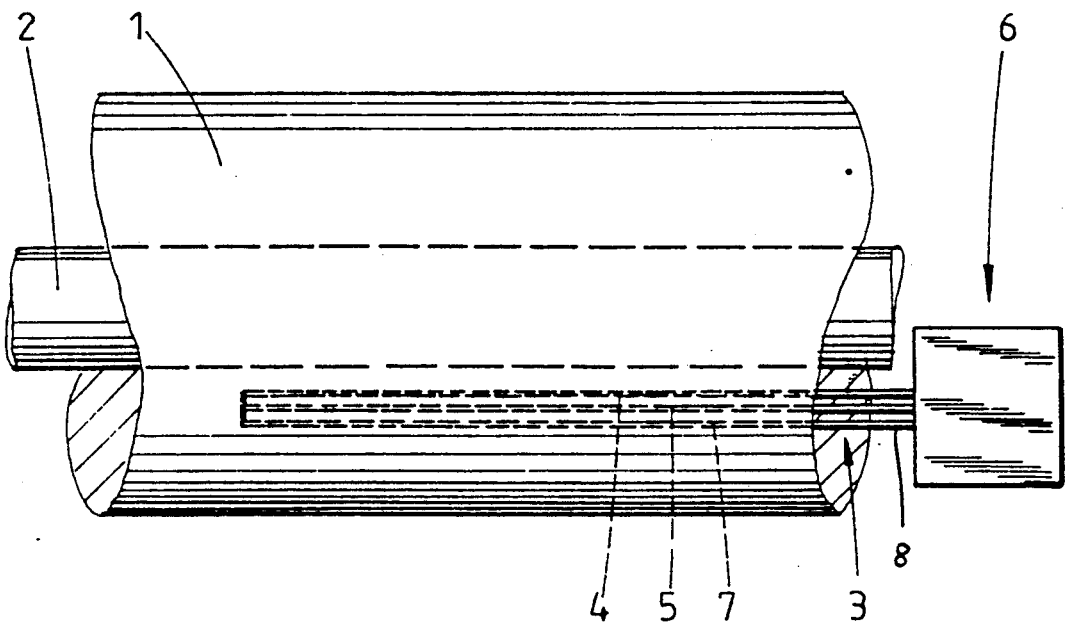

United States Patent [19]

Serwatzky

[11] Patent Number: 5,036,287
[45] Date of Patent: Jul. 30, 1991

[54] PROCEDURE AND DEVICE FOR CORROSION DETERMINATION

[75] Inventor: Günter Serwatzky, Grafschaft, Austria

[73] Assignee: Dipl.-Ing. Wrede & Niedecken Verwaltung GmbH, Fed. Rep. of Germany

[21] Appl. No.: 473,049

[22] Filed: Jan. 31, 1990

[30] Foreign Application Priority Data

Feb. 17, 1989 [DE] Fed. Rep. of Germany ....... 3904894

[51] Int. Cl.⁵ ............................................ G01R 27/08
[52] U.S. Cl. .................................... 324/700; 324/706; 324/718; 324/725; 324/71.2; 340/605
[58] Field of Search ............... 324/700, 699, 705, 706, 324/716, 718, 725, 71.2, 71.1; 340/605

[56] References Cited

U.S. PATENT DOCUMENTS

| | | | |
|---|---|---|---|
| 3,104,355 | 9/1963 | Holmes et al. | 324/700 X |
| 3,821,642 | 6/1974 | Seymour | 324/700 |
| 4,672,366 | 6/1987 | Butts | 340/605 |
| 4,703,253 | 10/1987 | Strommen | 324/700 |
| 4,703,254 | 10/1987 | Strommen | 324/700 |
| 4,922,232 | 5/1990 | Bosich | 340/605 |

Primary Examiner—Kenneth A. Wieder
Assistant Examiner—Robert W. Mueller
Attorney, Agent, or Firm—John F. A. Earley; John F. A. Earley, III

[57] ABSTRACT

A procedure and a device for determining corrosion of preferably insulated structural parts (2) assures in a simple way early detection of corrosion. For this purpose an electric conducting resistance wire (4) exposed to the same corrosive medium, e.g. condensation water, as the structural part (2) to be examined for corrosion is placed outside the structural part (2) and the electrical resistance of the resistance wire is measured. The effective cross-section of the resistance wire (4) and its electrical resistance change with the corrosion of the resistance wire (4) so that the resistance change of the resistance wire (4) registers the effect of the corrosive medium.

21 Claims, 1 Drawing Sheet

PROCEDURE AND DEVICE FOR CORROSION DETERMINATION

The invention concerns a procedure for determining corrosion of especially insulated structural parts and a device for determing corrosion of especially insulated structural parts, in particular for carrying out the procedure.

In the field of plant construction, especially in large industrial plants, numerous structural parts require sound, heat, or cold insulation. Flat structural parts and also pipelines or similar parts are included among these parts. For example, pipeline systems for the transport of cooling gas or liquid are usually both thermally and acoustically insulated, since both the heat losses during transport through the pipeline and the sounds emanating from it must be minimized. A corresponding insulation arrangement is known from DE 37 11 869 A1.

The insulation of structural parts, however, presents in practice many problems, since under or in the insulation coverings condensation water can form, for example, which can be removed only with difficulty. Especially with thermally insulated pipelines, as in a petrochemical plant, for example, condensation water forms very easily in the insulation or on the inner side of the insulation; this condensation water leads to corrosion that attacks the structural parts and pipelines from the outside. The DE 34 02 233 A1 therefore deals with the prevention of condensation on the one hand and with its removal on the other hand.

Practical experience has shown, however, that the formation of condensation beneath pipeline insulation can hardly be prevented and that moisture, once present in the insulation, is very difficult to remove. Consequently, it is only a question of time until the surface of the insulated structural parts—assuming that condensation takes place—begins to corrode. In order to avoid serious damage it is, therefore, important to recognize corrosive damage of structural parts of the abovementioned type right at the start, in order to replace the parts involved.

Thus, the task of the invention is to provide a procedure and a device for determining corrosion of specifically insulated structural parts by, or with, which an early recognition of corrosion is assured in a simple way.

The procedure according to the invention which satisfies the task just indicated comprises a procedure for determining corrosion preferably in insulated structural parts, in which there is placed on the outside of the section of the structural part to be monitored for corrosion an electric conducting resistance wire which is also exposed to the corrosive medium—condensation water, for instance—by determining the electric resistance of the resistance wire, whereby the effective cross-section changes in case of corrosion of the resistance wire, so that the change in resistance of the resistance wire registers the effect of the corrosive medium.

According to it, an electric conducting resistance wire is exposed to the corrosive medium in the area of the structural part to be monitored for corrison on the outside of the structural part, as well as on the inside of the insulation, if need be. The electrical resistance of the resistance wire is measured continuously or at specific time intervals by means of a corresponding circuit with an appropriate meter. Corrosion of the resistance wire changes the effective cross-section of the resistance wire, that is, it becomes smaller. The electrical resistance of the resistance wire changes or increases accordingly, and this registers the effect of a corrosive medium.

Advantageous arrangements of the procedure according to the invention include measuring the change of resistance of the resistance wire over a period of time and correlating the amount of change in the resistance with the degree of corrosion. The change in cross-section of the resistance wire serves for determining the place of corrosion. The resistance wire may be arranged directly next to the surface of the structural part to be checked for corrosion. The corrosive medium first attacks a protective layer surrounding the resistance wire and gradually, over a period of time, penetrates the protective wire and then attacks the resistance wire itself, after a delay. The retardation of corrosion occasioned by the nature and thickness of the protective covering is chosen in a way to make the retardation of the corrosion correspond to the time required for the corrosion medium to reach the structural part to be examined. The temperature influence on the electrical resistance of the reference wire not exposed to the corrosive medium because of suitable insulation to compensate for the temperature-dependent change in resistance of the resistance wire is metered and the change in resistance of the resistance wire relative to the reference wire registers the effect of the corrosive medium. The presence of an electric conducting corrosive medium is determined through the resistance wire working in combination with a conductor set up as a return line from the resistance wire and at the same time exposed to the corrosive medium in the area of the structural part, while the corrosive medium at the same time is producing an electric current flow from the resistance wire to the return line.

The degree of corrosion can also be determined by means of the procedure according to the invention procedure. This is done by measuring the change in resistance of the resistance wire caused by corrosion over a period of time, whereby the amount of change in resistance is correlated with the degree of corrosion.

Insofar as the resistance wire extends along the structural part to be examined for corrosion, the location of the corrosion could be located by means of the procedure according to the invention. The corrosion of the resistance wire could be located precisely also by use of ultrasound, for example.

The closer the resistance wire is placed to the surface of the part to be checked for corrosion, the better the resistance measurement of the resistance wire will reproduce the situation on the structural part under examination. On the other hand, if the resistance wire is placed somewhere in an insulation material relatively far from the structural part, determination of corrosion of the resistance wire will not prove that the structural part is also exposed to a corrosive medium.

It is especially advantageous when the corrosive medium does not touch the resistance wire directly, but first of all a protective layer covering the resistance wire. This protective layer is constituted in such a way that the corrosive medium gradually penetrates or dissolves it and only afterwards attacks the resistance wire itself—a delayed action. By choosing suitable conditions and thickness of the protective layer the retardation of corrosion—that is, the length of time from the attack of the corrosive medium on the protective covering to the beginning of corrosion of the resistance wire, can be made to correspond to the time during which the corrosive medium in the insulation has progressed from the resistance wire to the structural part. In such a case it is not necessary to place the resistance wire in immediate juxtaposition to the structural part. In any case, it must be seen to that the corrosive medium reaches first the resistance wire and then the structural part.

Since the resistance of the resistance wire depends also on the immediate surrounding temperature and consequently on the temperature of the resistance wire itself, in order to compensate for a change in resistance dependent upon a change in temperature of the resistance wire the actual influence of the temperature should be determined. For this purpose the influence of the temperature on the eletrical resistance of a reference resistance wire, which by means of suitable insulation is not exposed to the corrosive medium, is determined. The change in resistance of the resistance wire relative to the reference wire then indicates the effect of the corrosive medium.

Absolute values between the resistance of the resistance wire and the resistance of the reference wire are not necessary for identifying corrosion, only a recognizable, relative change in resistance, indicating corrosion, is required. If, however, the degree of corrosion is to be determined also, then the amount of change of resistance is a measure of the degree of corrosion.

The presence of a corrosive medium which conducts electricity can be determined by the working together of the resistance wire with a conductor inserted as a return line of the resistance wire exposed to the corrosion in the area of the structural part to be checked. The electric conducting corrosive medium causes an additional amount to flow from the resistance wire to the return line, in other words, a sort of short circuit, which has an effect on the total resistance of the conductor set-up. In this regard it is essential not to insulate the return line from the corrosive medium. The device according to the invention for determining corrosion of especially insulated structural parts includes a sensor with a resistance wire and a return line for the resistance wire, as well as a current-measuring arrangement for determining the resistance of the resistance wire. Simple means—a resistance wire in which the resistance increases as its cross-section is reduced by corrosion and a corresponding measureing device—make it possible to report reliably the beginning of corrosion, whereby the corrosion of the resistance wire will register corrosion of the structural part being checked.

There are various possiblities for constructing and extending this invention in an advantageous way. Please refer to the following explanation of just one mode of renditon of the device according to the invention together with the drawing. Generally preferred elaborations of the concept are also explained in connection with the explanation of the preferred mode of renditon of the device according to the invention and the relative drawing.

In the drawing shown:

FIG. 1. A schematic representation of the arrangement of the device accordingto the invention in the insultation of a pipeline and FIG. 2. A block schematic of a mode of rendition of the device according to the invention.

FIG. 1 shows schematically a device according to the invention for determining corrosion of an insulated structural part, namely, of a pipeline (2) provided with insulation (1). A sensor (3) is equipped with a resistance wire (4) and a return line (5) for the resistance wire (4). The sensor (3), the resistance wire (4) and the return line (5) are connected to a measuring device (6), that will be explained more precisely later, in order to determine the resistance of the resistance wire (4). FIG. 1 shows clearly that the sensor (3) is situated more or less parallel to the pipeline (2).

In order for the sensor (3) or the resistance wire (4) to determine the condition of the pipe surface extremely accurately it is an advantage if the resistance wire (4) is made of a material which either exhibits the same corrosion behavior as the pipeline (2) under observation or is made of the same material as pipeline (2). In any case it must be made certain that the pipeline (2) and the resistance wire (4) become corroded after about the same exposure time under certain atmospheres.

In FIG. 1 the sensor (3) is situated very close to the pipeline under observation. If the corrosive medium inside the insulation (1) moves radially, from outside toward inside, then the corrosive medium will first reach the sensor (3) and only afterwards the pipeline (2). The invention device would therefore register corrosion too soon or it would have to be placed directly on the pipeline (2) surface.

Help for this problem is provided by a covering of the resistance wire—not shown in the figures—which permits the corrosive medium, e.g., condensation water, to penetrate to the resistance wire itself only after a certain exposure time, that is, a time governed by the thicknesss and nature of the layer of the covering. The exposure time, as well as the delay of the beginning of corrosion resulting from it, would then have to be measured in such a way that the corrosive medium will have moved on to the pipeline, so that corrosion of the resistance wire and of the pipe surface will commence at the same time.

In order to provide the covering of the resistance wire with the abovementioned properties the covering could be made of a semi-permeable material, a synthetic one for example. This synthetic material could be applied by an injection molding process or plasma spray in the desired thickness.

A further advantageous alternative example of a covering delaying the resistance wire corrosion would be in making the resistance wire covering soluble in the corrosive medium. In this way the corrosive medium could attack the resistance wire only after dissolving its covering. Such a covering could be applied as a lacquer.

Initially, the return line (5) serves to connect the resistance wire (4) to the measuring instrument (6) and, secondarily, to determine whether an electric conducting liquid is present as a corrosive medium. Therefore, the return line (5) is directly exposed to the corrosive medium, whereby an electric conducting liquid causes an additional current flow between the resistance wire (4) and the return line (5) which in turn produces a diminution in the resistance of the circuit containing the resistance wire (4) and the return line (5). The return line could also be surrounded by an electric conducting synthetic material layer to protect it from corrosive media. An example of this could be an acid- and base-resistant carbon-containing synthetic material.

FIGS. 1 an 2 together show that the return line (5) has the same length as the resistance wire (4). In this way the presence of electric conducting liquids in the area of the entire resistance wire (4) can be determined. Such an elaboration of the resistance wire is therefore especially suited for locating the place of corrosion, as well as for indicating the location of moisture.

Figure 2:
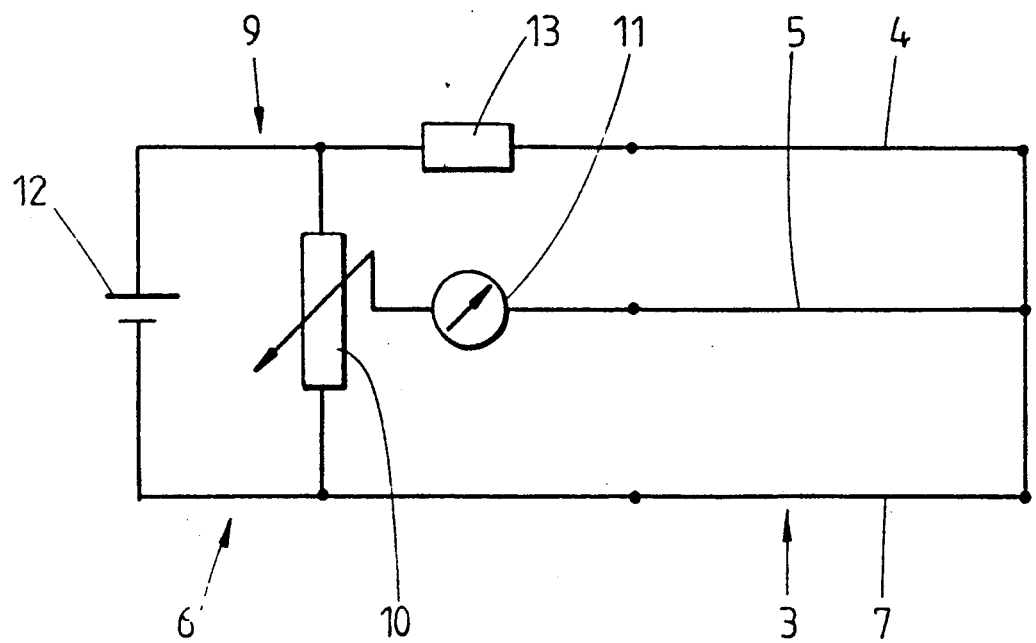

Since the resistance of the resistance wire (4) varies also according to changes in temperature, and such a change in resistance could cancel out the change in resistance caused by corrosion, a reference wire (7) is provided appropriately to compensate for the temperature-dependent change in the resistance of the resistance wire (4). The reference wire (7) belongs to the sensor (3) and is protected from corrosion by suitable insulation (8). FIG. 2 shows clearly that both the reference wire (7) and the resistance wire (4) are connected to the return line (5). The resistance of the reference wire (7) is likewise determined by the measuring instrument (6) and depends exclusively on the length and material of the reference conductor (7) and the temperature. The change in resistance of the resistance wire (4) in relation to the reference wire (7) registers the effect of the corrosive medium.

FIGS. 1 and 2 also show that the reference wire (7) has the same length as the resistance wire (4). The wires forming the sensor (3): resistance wire (4), return line (5), and reference wire (7), have all together the same length snd extend in the model shown in FIG. 1 along pipeline (2) in an area defined by the length of the sensor (3). Accordingly, it is entirely possible that in the case of structural parts of limited size a sensor may be used that checks the entire length of such a structural part for corrosion.

To compensate for the influence of temperature on the electrical resistance of the resistance wire the reference wire should be made of the same material as the resistance wire, so that the temperature influences on the resistance wire and the reference wire will agree absolutely.

FIG. 2 shows in diagram form a mode of rendition of the device according to the invention. The sensor (3) and the measuring device (6) are components of a wheatstone bridge (9). The Wheatstone bridge (9) shows a resistor to be measured, a known resistor, a potentiometer (10), a signalling apparatus in the form of a galvanometer (11), and a voltage source (12). The resistance wire (4) of the sensor (3) is the resistor to be measured and the reference wire (7) of the sensor (3) is the known resistor of the Wheatstone bridge. In addition, a resistor (13) is provided for rough balancing the bridge.

The return line (5) leads from the resistance wire (4) and the reference wire (7) to the galvanometer (11) and from there to the potentiometer (10), which can be set up as a linear wire potentiometer.

The manner of operation may be summarized as follows: The resistance wire (4) changes its resistance on the one hand because of a change in temperature, on the other hand because of a diminution in the cross-section caused by corrosion. The reference wire (7) changes its resistance only because of a change in temperature, since it is protected from corrosion by its insulation (8). Consequently the change in resistance produced by the change in temperature is compensated for in the Wheatstone bridge (9).

For the principles of calculation of the "unknown" resistance in Wheatstone bridge circuits see in particular KRAfTFAHRTECHNISCHES TASCHENBUCH (MOTOR VEHICLE TECHNICAL POCKET MANUAL), Bosch, VDI-Verlag GmbH, Düsseldorf, 19. Auflage (Edition), 1984, p. 105, below right.

The coverings of the resistance wire and of the return wire can both be made of a dielectric.

I claim:

1. A procedure for the determination of corrosion preferably in insulated structural parts, in which there is placed in distant relationship to the outside of the section of the structural part to be monitored for corrosion an electric conducting resistance wire, surrounded by a protective layer, which is also exposed to the corrosive medium—condensation water, for instance—by determining the electric resistance of the resistance wire, whereby the effective cross-section changes in case of corrosion of the resistance wire, so that change in resistance of the resistance wire registers the effect of the corrosive medium, in which the corrosive medium first attacks the protective layer surrounding the resistance wire and gradually, over a period of time, penetrates the protective layer and then attacks the resistance wire itself, in which the retardation of corrosion occasioned by the nature and thickness of the protective layer is chosen in a way to make the retardation of the corrosion correspond to the time required for the corrosion medium to reach the structural part to be examined.

2. A procedure according to claim 1, in which the resistance wire is arranged directly next the surface of the structural part to be checked for corrosion.

3. A procedure according to claim 1, in which the temperature influence on the electrical resistance of a reference wire not exposed to the corrosive medium because of suitable insulation to compensate for the temperature-dependent change in resistance of the resistance wire is metered and whereby the change in resistance of the resistance wire relative to the reference wire registers the effect of the corrosive medium.

4. A procedure according to claim 3, in which the presence of an electric conducting corrosive medium is determined through the resistance wire working in combination with a conductor set up as a return line from the resistance wire and at the same time exposed to the corrosive medium in the area of the structural part, while the corrosive medium at the same time is producing an additional current flow from the resistance wire to the return line.

5. A device for the determination of corrosion of preferably insulated structural parts, in particular for carrying out the procedure of claim 1, with a sensor equipped with a resistance wire, return line from the resistance wire and a measuring instrument for determining the resistance of the resistance wire in which the resistance wire is equipped with a protective layer which permits the corrosive medium e.g., condensation water, to penetrate to the resistance wire itself only after a certain period of activity, that is, after a period of time conditioned by the thickness and nature of the protective layer.

6. A device according to claim 5, in which the resistance wire is made of a material which exhibits about the same corrosion behavior as the structural part being examined for corrosion.

7. A device according to claim 5, in which the resistance wire is made of the same material as the structural part being examined for corrosion.

8. A device according to claim 5, in which the protective layer of the resistance wire comprises a semipermeable material.

9. A device according to claim 8, in which the semipermeable material comprises a synthetic material.

10. A device according to claim 5, in which the protective layer of the resistance wire is soluble in the corrosive medium.

11. A device according to claim 5, in which the return line is directly exposed to the corrosive medium.

12. A device according to claim 11, in which the return line has the same length as the resistance wire.

13. A device according to claim 5, in which the return line is surrounded by a carbon-containing electric conducting synthetic covering.

14. A device according to claim 5, in which in order to compensate for a temperature-dependent change in resistance of the resistance wire the sensor is equipped with a reference wire protected from corrosion by suitable insulation and also connected to the return wire, so that its electrical resistance, to be determined preferably by the measuring instrument, depends exclusively on the length and the material of the reference wire, as well as on the temperature of the environment, and the change in resistance of the resistance wire registers the effect of the corrosive medium relative to the reference wire.

15. A device according to claim 14, in which the reference wire has the same length as the resistance wire.

16. A device according to claim 14, in which the reference wire is made of the same material as the resistance wire.

17. A device according to claim 14, in which for the purpose of measuring resistance a bridge circuit is set up as a Wheatstone bridge equipped with an unknown resistor, that is, one to be measured, a known resistor, a potentiometer, a registering device - preferably a galvanometer and a voltage source, and in which the resistance wire of the sensor is the resistor to be measured and the reference wire of the sensor is the known resistor of the Wheatstone bridge.

18. A device according to claim 17, in which the potentiometer is a linear wire potentiometer is a linear wire potentiometer.

19. A device according to claim 5, in which the sensor extends essentially over the entire length of the structural part being examined.

20. A process for determining corrosion of insulated structural parts comprising the steps of placing an electrical conducting resistance wire in distant relationship to the outside of the section of the structural part that is desired to be monitored for corrosion due to being in contact with a corrosive medium, said electrical conducting resistance wire being surrounded by a protective layer; said protective layer being gradually penetrable by the corrosive medium, exposing the electrical conducting resistance wire with its protective layer to the same corrosive medium contacting the outside of the section of the structural part being monitored for corrosion, determining the electrical resistance of the electrical conducting resistance wire, and determining any changes in resistance of the electrical conducting resistance wire due to the corrosive medium for corroding the electrical conducting resistance wire.

21. The process of claim 20, further including measuring changes in resistance of the resistance wire over a period of time, correlating the amount of change in resistance of the resistance wire with the degree of corrosion, arranging the resistance wire directly next to the surface of the structural part that is desired to be checked for corrosion, providing the resistance wire with a protective layer that gradually over a period of time is penetrated by the corrosive medium, retarding corrosion of the resistance wire with the protective layer such that the corrosion medium simultaneously reaches the resistance wire and the structural part being monitored, compensating for temperature-dependent changes in resistance of the resistance wire by measuring the change in resistance of a reference wire not exposed to the corrosive medium due to the reference wire being insulated therefrom and comparing the change in resistance of the resistance wire relative to the change in resistance of the reference wire, and determining the presence of an electrical conducting corrosive medium by measuring the change in the resistance of a circuit containing the resistance wire and a return line directly exposed to the corrosive medium.

* * * * *